US008916151B2

(12) United States Patent
Genkin et al.

(10) Patent No.: US 8,916,151 B2
(45) Date of Patent: *Dec. 23, 2014

(54) METHOD FOR TREATING A REDUCTION OF FERTILITY

(75) Inventors: Dmitry Dmitrievich Genkin, Saint-Petersburg (RU); Viktor Veniaminovich Tets, Saint-Petersburg (RU); Georgy Viktorovich Tets, Saint-Petersburg (RU)

(73) Assignee: CLS Therapeutics Limited, Guernsey, Channel Islands (GB)

( * ) Notice: Subject to any disclaimer, the term of this patent is extended or adjusted under 35 U.S.C. 154(b) by 714 days.

This patent is subject to a terminal disclaimer.

(21) Appl. No.: 11/919,141

(22) PCT Filed: Apr. 25, 2005

(86) PCT No.: PCT/RU2005/000236
§ 371 (c)(1),
(2), (4) Date: Oct. 23, 2007

(87) PCT Pub. No.: WO2006/130034
PCT Pub. Date: Dec. 7, 2006

(65) Prior Publication Data
US 2009/0053200 A1      Feb. 26, 2009

(51) Int. Cl.
C07K 16/44      (2006.01)

(52) U.S. Cl.
CPC ..................................... C07K 16/44 (2013.01)
USPC ...................................................... 424/130.1

(58) Field of Classification Search
None
See application file for complete search history.

(56) References Cited

U.S. PATENT DOCUMENTS

| 4,485,095 | A | 11/1984 | Fujisaki et al. |
| 5,484,589 | A | 1/1996 | Salganik |
| 5,656,589 | A | 8/1997 | Stossel et al. |
| 5,855,920 | A | 1/1999 | Chein |
| 5,889,153 | A | 3/1999 | Suzuki et al. |
| 5,952,170 | A | 9/1999 | Stroun et al. |
| 6,033,846 | A | 3/2000 | Fournie |
| 6,156,504 | A | 12/2000 | Gocke et al. |
| 6,391,607 | B1 | 5/2002 | Lazarus et al. |
| 6,428,785 | B1 | 8/2002 | Gokeen |
| 6,455,250 | B1 | 9/2002 | Aguilera et al. |
| 6,465,177 | B1 | 10/2002 | Hoon |
| 6,521,409 | B1 | 2/2003 | Gocke et al. |
| 7,402,724 | B2 | 7/2008 | Conover |
| 7,612,032 | B2 * | 11/2009 | Genkin et al. ................... 514/2 |
| 2003/0044403 | A1 | 3/2003 | Shak |
| 2004/0001817 | A1 | 1/2004 | Giampapa |
| 2004/0157239 | A1 | 8/2004 | Tanuma et al. |
| 2006/0228347 | A1 | 10/2006 | Sunaga et al. |
| 2006/0233780 | A1 | 10/2006 | Genkin et al. |
| 2007/0104702 | A1 | 5/2007 | Genkin et al. |
| 2008/0004561 | A1 | 1/2008 | Genkin et al. |
| 2009/0047272 | A1 | 2/2009 | Appelbaum et al. |
| 2010/0061971 | A1 | 3/2010 | Genkin et al. |
| 2010/0150903 | A1 | 6/2010 | Genkin et al. |
| 2010/0303796 | A1 | 12/2010 | Genkin et al. |
| 2011/0033438 | A1 | 2/2011 | Bartoov et al. |
| 2011/0070201 | A1 | 3/2011 | Shaaltiel et al. |
| 2011/0189156 | A1 | 8/2011 | Genkin et al. |

FOREIGN PATENT DOCUMENTS

| CA | 2394856 | 6/2001 |
| CA | 2184582 | 12/2001 |
| DE | 4024530 | 2/1992 |
| DE | 10221194 | 12/2003 |
| EP | 0325191 | 7/1989 |
| EP | 1655036 | 5/2006 |
| EP | 1661579 | 5/2006 |
| EP | 1666055 | 6/2006 |
| EP | 2095825 | 9/2009 |
| GB | 984464 | 2/1965 |
| GB | 1005985 | 9/1965 |
| JP | 61293927 | 12/1986 |
| JP | 2006-290769 | 10/2006 |
| NZ | 299257 | 8/2000 |
| RU | 2099080 | 12/1997 |
| RU | 2001129826/14 | 11/2001 |
| RU | 2001104426 | 1/2003 |
| RU | 2202109 | 4/2003 |
| RU | 2207876 | 7/2003 |
| RU | 2003127898/14 | 9/2003 |
| RU | 2239404 | 11/2004 |
| RU | 2239442 | 11/2004 |
| RU | 2267329 | 1/2006 |
| RU | 2269356 | 2/2006 |
| RU | 2269357 C2 | 2/2006 |
| RU | 2269358 | 2/2006 |
| RU | 2269359 | 2/2006 |
| RU | 2308968 | 10/2007 |

(Continued)

OTHER PUBLICATIONS

Sugihara et al. Br. J. Cancer, 1993, 67:66-70.*
Irvine et al. Journal of Andrology, 2000, 21:33-44.*
Valerian E. Kagan et al. Toward Mechanism-based Antioxidant Interventions 2002 pp. 188-198.
Stephen D. Hursting et al. Calorie Restriction, Aging and Cancer Prevention: Mechanisms of Action and Applicability to Humans 2003 pp. 131-152.
Judith Campisi Cancer and Ageing: Rival Demons? May 2003 pp. 339-349.
Ana Krtolica et al. Senescent Fibroblasts Promote Epithelial Cell Growth and Tumorigenesis: A Link Between Cancer and Aging Aug. 14, 2001 pp. 12072-12077.

(Continued)

Primary Examiner — Sharon Wen
(74) Attorney, Agent, or Firm — Troutman Sanders LLP

(57) ABSTRACT

The present invention provides a method for retarding unhealthy manifestations brought by ageing of human beings (in particular, but not limited to the reduction of sexual activity and fertility, climax, changes in glucose tolerance, reduction of cognitive and mnestic functions, reduction of stress resistance, development of organ and tissue sclerosis). According to the invention this task is solved by administration into the blood circulation of an agent which inactivates extracellular blood plasma DNA.

5 Claims, 1 Drawing Sheet

(56) References Cited

FOREIGN PATENT DOCUMENTS

| WO | WO93/03709 | 3/1993 |
| WO | WO95/00170 | 1/1995 |
| WO | WO97/28266 | 8/1997 |
| WO | WO97/47751 | 12/1997 |
| WO | PCT/US99/27907 | 11/1999 |
| WO | WO00/03709 | 1/2000 |
| WO | WO00/31238 | 6/2000 |
| WO | WO01/74905 | 10/2001 |
| WO | WO03/068254 | 8/2003 |
| WO | WO2005004789 | 1/2005 |
| WO | WO2005004903 | 1/2005 |
| WO | WO2005004904 | 1/2005 |
| WO | WO2005007187 | 1/2005 |
| WO | WO2005/115444 | 12/2005 |
| WO | WO2008047364 A2 | 4/2008 |
| WO | WO2008/066403 | 6/2008 |
| WO | WO2011/073665 | 6/2011 |
| WO | WO2012/075506 | 6/2012 |
| WO | WO2014/020564 A1 | 2/2014 |

OTHER PUBLICATIONS

N. I. Arinchina et al. Cellular and Humoral Mechanisms of Immunity Changing 1982 pp. 280-282.

Jean-Philippe Coppe et al. Secretion of Vascular Endothelial Growth Factor by Primary Human Fibroblasts at Senescence Apr. 6, 2006 pp. 29568-29574.

Simon Parrinello et al. Stromal-epithelial Interactions in Aging and Cancer: Senescent Fibroblasts alter Epithelial Cell Differentiation Nov. 4, 2004 pp. 485-496.

Calvin B. Harley Telomere Loss: Miotic Clock or Genetic Time Bomb? Jul. 23, 1991 pp. 271-281.

Judith Campisi et al. Cellular Senescence: When Bad Things Happen to Good Cells Aug. 1, 2007 pp. 729-740.

J.F. Whitfield et al. The Effects of X-Radiation on Lactate Metabolism of Mammalian Cells May 13, 1964 p. 637.

L. Hayflick et al. The Serial Cultivation of Human Diploid Cell Strains May 15, 1961 pp. 585-621.

L. Hayflick Aging Under Glass May 13, 1970 Dept. of Medical Microbiology, Stanford University School of Medicine Apr. 13, 1970 pp. 291-303.

L. Hayflick The Limited In Vitro Lifetime of Human Diploid Cell Strains May 4, 1964 pp. 614-635.

Kaprin et al., Prognoz i lechenie bol'nih poverhnostnim rakom mochevogo puziria visokoi stepeni riska, Visokie Tehnologii v Onkologii, Rostov-na-Donu, vol. 3, pp. 149-150, 2000 (Reference in Russian and English-language translation).

Dayan, Pharmacological-Toxicological (Expert Report on Recombinant Human Deoxyribonuclease I (rhDNase; Pulmozyme™), Hum. Exp. Toxicol., 13: S2, 1994.

Roche, Pulmozyme®, Dornase alfa solution for inhalation 1.0 mg/ml, Data Sheet, 2008.

Varidase Buccal Tablets product information from Lederle Laboratories Inc., Canad. M. A. J., vol. 84, pp. 867-868, 1961.

European Office Action, dated Jun. 12, 2013, which issued during the prosecution of European Patent Application No. 05745412.6, which corresponds to the present application.

Prince, W.S., et al, Pharmacodynamics of Recombinant Human DNASE I in Serum, Clin Exp Immunol, vol. 113, pp. 289-296, 1998.

Rowlatt, C., et al., Lifespan, Age Changes and Tumour Incidence in an Ageing C57BL Mouse Colony, Laboratory Animals, vol. 10, pp. 419-442, 1976.

Riches, A.C., et al., Blood Volume Determination in the Mouse, J. Physiol., vol. 228, pp. 279-284, 1973.

Favorov, P.V. Issledovaniye kinetiki prevrashchenii DNK pod deistviem DNK-topoizomeraz i DNK-abzimov, author's abstract of PhD thesis in biological sciences, M., pp. 3-4, 1999 (Reference in Russian and English-language translation).

Gluhov BM, Znachenije nukleaz v patogeneze neirovirusnyh zabolevanij, Avtoreferat dissertatsii na soiskanie uchenoi stepeni doktora medicinskikh nauk (author's abstract of MD thesis in medical sciences), Novosibirsk, pp. 15-16, 21-26, 1996 (Reference in Russian and English-language translation of pp. 14-17 and 20-27).

Kalandarishvili F., Nakoplenie spontanno povrezhdennoj DNK v nei postgepatjektomirovannoj pecheni u staryh krys, Med. Novosti Gruzii, No. 5, pp. 11-12, 1998 (Reference in Russian and English-language translation).

Mel'Nikov D, et al., Voprosy onkologicheskoi pomoschi na etape reformirovaniya zdravookhraneniya, Ekaterinburg, pp. 159-161, 1996 (Reference in Russian and English-language translation).

Nikolenko G. N., Sozdanie rekombinantnykh antitel 17 protiv virusa kleschevogo entsefalita i izuchenie ikh svoystv, Avtoreferat dissertatsii na soiskanie uchenoi stepeni kandidata biologicheskikh nauk (author's abstract of PhD thesis in biological sciences), Koltsovo, pp. 1-2, 19, 1999 (Reference in Russian and English-language translation).

Osivac et al., Reorganizacija DNK i biologicheskoje starenije, Biohimija, vol. 62, pp. 1491-1502, 1997 (Reference in Russian and English-language translation).

Perel'Man MI, et al., Molekuljarnaja medicina i lechenie tuberkuleza, Problemi tuberkuleza, No. 5, pp. 5-7, 2001 (Reference in Russian and English-language translation).

Translation of International Preliminary Report on Patentability for PCT/RU2005/000236, mailed Feb. 13, 2008.

Yastrebova N.E., Razrabotka i izuchenie diagnosticheskikh vozmozhnostei immunofermentnykh test-sistem na osnove antigennykh preparatov zolotistogo stafilokokka i DNK, Avtoreferat dissertatsii na soiskanie uchenoi stepeni kandidata meditsinskikh nauk (author's abstract of PhD thesis in medical sciences), M., pp. 17-18, 1988 (Reference in Russian and English-language translation).

Rowe P., Comhaire F. Hargreave T. Mellows H., WHO Manual for the Standardized Investigation and Diagnosis of the Infertile Couple, Cambridge University Press, 1993, 83 p.

WHO Laboratory Manual for the Examination of Human Semen and Sperm-cervical Mucus Interaction, 4th ed., Cambridge University Press, 1999, 128 p.

Canudas-Romo, Vladimir, "Three Measures of Longevity: Time Trends and Record Values", Demography 2010; 47(2):299-312.

Schmitz, Kathryn H., et al., "The Intersection of Cancer and Aging: Establishing the Need for Breast Cancer Rehabilitation", Cancer Epidemiol Biomarkers Prev 2007; 16(5):866-872.

Kenyon, Cynthia, "A Conserved Regulatory System for Aging", Cell 2001; 105:165-168.

National Institute on Aging, "Can We Prevent Aging? Tips from the National Institute on Aging", Feb. 2012; pp. 1-8.

Anker, P. et al., Tumor-related alterations in circulating DNA, potential for diagnosis, prognosis and detection of minimal residual disease, Leukemia, 15, 289-91, 2001.

Ashton, G., Growing pains for biopharmaceuticals, Nature Biotech, vol. 19, pp. 307-311, 2001.

Aung et al., Current status and future potential of somatic mutation testing from circulating free DNA in patients with solid tumours, HUGO J, vol. 4, pp. 11-21, 2010.

Botto, N., et al., Elevated levels of oxidative DNA damage in patients with coronary artery disease, Coronary Artery Disease, vol. 13, pp. 269-274, 2002.

Boyko et al., Cell-free DNA—a marker to predict ischemic brain damage in a rat stroke experimental model, Journal of Neurosurgical Anesthesiology, vol. 23, pp. 222-228, 2011.

Burt et al., Detection of circulating donor deoxyribonucleic acid by microsatellite analysis in a liver transplant recipient, Liver Transpl Surg, vol. 2, pp. 391-394, 1996.

Davis JC et al., Recombinant human Dnase I (rhDNase) in patients with lupus nephritis, LUPUS, vol. 8, pp. 68-76, 1999.

Deitsch, et al., Transformation of malaria parasites by the spontaneous uptake and expression of DNA from human erythrocytes, Nucleic Acids Research, vol. 29, pp. 850-853, 2000.

Deocharan B., et al., Alpha-actinin is a cross-reactive renal target for pathogenic anti-DNA antibodies, J. Immunol., vol. 168, pp. 3072-3078, 2002.

Department of Health and Human Services Food and Drug Administration, Federal Register, Dec. 13, 1985, vol. 50, No. 240.

(56) References Cited

OTHER PUBLICATIONS

Dittmar, Manuela et al., A novel mutation in the DNASE1 gene is related with protein instability and decreased enzyme activity in thyroid autoimmunity, Journal of Autoimmunity, vol. 32, pp. 7-13, 2009.
El Hassan No, et al. Rescue use of Dnase in critical lung atelectasis mucus retention in premature neonates, Pediatrics., vol. 108, pp. 468-470, 2001.
Extended European Search Report for European Patent Appl. No. EP12170750 dated Aug. 3, 2012.
Extended European Search Report for European Patent Appl. No. EP12170754 dated Aug. 3, 2012.
Extended European Search Report for European Patent Appl. No. EP12170757 dated Aug. 3, 2012.
Freshney, R. I., Culture of Animal Cells, a Manual of Basic Technique, Alan R. Liss, Inc., New York, pp. 3-4, 1983.
Funakoshi, A, et al., Clinical Investigation of Serum Deoxyribonuclease: II. Clinical Studies of Serum Deoxyribonuclease Activity in Pancreatic Disease, Gastroenterologia Japonica, vol. 14, pp. 436-440, 1979.
Gannushkina, LV., et al., Plasma DNA Levels in Patients with Atherosclerotic Involvement of the Major Arteries of the Head and lateral Amyotrophic Sclerosis, Bulletin of Experimental Biology and Medicine, vol. 124, pp. 1164-1166, 1997 (Translated from: Gannushkina LV. et al., 'Uroven DNK v plazme krovi bolnykh s arteroskroticheskim porazheniem magistralnykh artery golovy I bokovym amiotroficheskim sklerozom, Byulleten' Experimental'noi Biologii i Meditsiny, Moscow, Meditsina, No. 12, pp. 610-612, 1997).
Gibbs et al., Mechanism-Based Target Identification and Drug Discovery in Cancer Research Science, vol. 287, pp. 1969-1973, 2000.
Gormally et al., Circulating free DNA in plasma or serum as biomarker of carcinogenesis: Practical aspects and biological significance, Mutation Research, vol. 635, pp. 105-117, 2007.
Gorrini, C., et al., Effect of apoptogenic stimuli on colon carcinoma cell lines with a different c-myc expression level, Int J Mol Med, vol. 11, pp. 737-742, 2003.
Gura, T., Systems for Identifying New Drugs Are Often Faulty, Science, vol. 278, pp. 1041-1042, 1997.
Hann, et al. Building 'validated' mouse models of human cancer. Curr Opin Cell Biol, vol. 13, pp. 778-784, 2001.
Horlitz, M., et al., Optimized Quantification of Fragmented, Free Circulating DNA in Human Blood Plasma Using a Calibrated Duplex Real-Time PCR, PLoS ONE, vol. 4, Issue 9, e7207, 2009.
Huttunen, R., et al., Fatal Outcome in Bacteremia is Characterized by High Plasma Cell Free DNA Concentration and Apoptotoc DNA Fragmentation: A Prospective Cohort Study, PLoS ONE, vol. 6, e21700, 2011.
International Search Report for PCT/RU2003/000304, mailed on Mar. 25, 2004.
International Search Report for PCT/RU2004/000260, mailed on Dec. 9, 2004.
International Search Report for PCT/RU2004/000261, mailed on Oct. 21, 2004.
International Search Report for PCT/RU2004/000262, mailed on Oct. 21, 2004.
International Search Report for PCT/RU2005/000236, mailed on Nov. 24, 2005.
International Search Report for PCT/RU2006/000642, mailed on Aug. 2, 2007.
Juncosa, B., DNA on the Loose: Next-Gen Blood Tests Tap Free-Floating Genetic Material, Scientific American, Mar. 18, 2009.
Jylhava et al., Aging is associated with quantitative and qualitative changes in circulating cell-free DNA: the Vitality 90+ study, Mechanisms of Ageing and Development, vol. 132, pp. 20-26, 2011.
Kawane, K, et at, DNAse II deficiency causes chronic polyarthritis in mice, Nature Clinical Practice Rheumatology, vol. 3, p. 192, 2007.
Krapf F. et al., The estimation of circulating immune complexes, C3d, and anti-ds-DNA-antibody serum levels in the monitoring of therapeutic plasmapheresis in a patient with systemic lupus erythematosus. A case report, Clin Exp Rheumatol., vol. 3, pp. 159-162, 1985.
Lachmann PJ, Lupus and Desoxyribonuclease, Lupus, vol. 12, pp. 202-206, 2003.
Lecompte, et al., Detection of free-circulating tumor-associated DNA in plasma of colorectal cancer patients and its association with prognosis, Int. J. Cancer, vol. 100, pp. 542-548, 2002.
Lee, D., Continued Marketing of a Useless Drug ('Varidase') in Panama, Lancet, March, vol. 335, p. 667, 1990.
Leland et al., Cancer chemotherapy—ribonucleases to the rescue, Chem. & Bio., vol. 8, pp. 405-413, 2001.
Leon et al., Free DNA in the Serum of Cancer Patients and the Effect of Therapy, Cancer Research, vol. 37, pp. 646-650, 1977.
Li et al., The *Haemophilus ducreyi* cytolethal distending toxin activates sensors of DNA damage and repair complexes in proliferating and non-proliferating cells, Cellular Microbiology, vol. 4, pp. 87-99, 2002.
Liggett et al., Methylation patterns of cell-free plasma DNA in relapsing-remitting multiple sclerosis, Journal of Neurological Sciences, vol. 290, pp. 16-21, 2010.
Macanovic et al., The treatment of systemic lupus-erythematosus (SLE) in NZB/W F1-hybrid mice-studies with recombinant murine DNase and with dexamethasone, Clinical and Experimental Immunology, vol. 106, pp. 243-252, 1996.
Malickova, Karin et al., Decreased Activity of DNase-I Predisposes to Immune-Mediated Complications in IBD Patients During Anti-TNFA Treatment, Gastroenterology, Abstract 202, vol. 138 (5 Supplement 1), S-37, 2010.
Maurer, HR, Bromelain: biochemistry, pharmacology and medical use, Cell Mol. Life. Sci., vol. 58, pp. 1234-1245, 2001.
Merkus et al., DNase treatment for atelectasis in infants with severe respiratory syncytial virus bronchiolitis, Eur Respir J, vol. 18, pp. 734-737, 2001.
Moreira VG et al., Usefulness of cell-free plasma DNA, procalcitonin and C-reactive protein as markers of infection in febrile patients, Annals of Clinical Biochemistry, vol. 47, pp. 253-258, 2010.
Mosca et al., Cell-free DNA in the plasma of patients with systemic sclerosis, Clinical Rheumatology, vol. 28, pp. 1437-1440, 2009.
Mutirangura A., Serum/plasma viral DNA: mechanisms and diagnostic applications to nasopharyngeal an cervical carcinoma, Ann NY Acad Sci., vol. 945, pp. 59-67, 2001.
Nestle & Roberts, An extracellular nuclease from *Serratia marcescens*, J. Biol. Chem., vol. 244, pp. 5213-5218, 1969.
Ngan et al., Remarkable Application of Serum EBV EBER-1 in Monitoring Response of Nasopharyngeal Cancer Patients to Salvage Chemotherapy, Ann. NY Acad. Sci., vol. 945, pp. 73-79, 2001.
Oliven et al., Orally and Rectally Administered Streptokinase, Pharmacology, vol. 22, pp. 135-138, 1981.
Pisetsky, D., Immune response to DNA in systemic lupus erythematosus, Isr. Med. Assoc. J., vol. 3, pp. 850-853, 2001.
Pressler T., Review of recombinant human deoxyribonuclease (rhDNase) in the management of patients with cystic fibrosis, Biologics: Targets & Therapy, vol. 2, pp. 611-617, 2008.
Pulmozyme® (dornase alfa) Inhalation Solution product leaflet, Genetech, Inc., 2005.
Rao KS and Shrivastaw KP, Studies on the synthesis and degradation of DNA in developing and old chick cerebellum, Journal of Neurochemistry, vol. 27, pp. 1205-1210, 1976.
Raz E. et al., Anti-DNA antibodies bind directly to renal antigens and induce kidney dysfunction in the isolated perfused rat kidney, J Immunol, vol. 142, pp. 3076-3082, 1989.
Schapira, Anthony H. V., Mitochondrial disease, Lancet, vol. 368, pp. 70-82, 2006.
Sergeeva L. M., Kliniko-laboratonaya otsenka mukoliticheskogo effekta pulmozima u bolnykh mukovistsidozom, Ekaterinburg, 1999, PhD dissertation in medicine, p. 9, paragraphs 2-3; p. 12, paragraph 4; p. 13, paragraphs 1-2; p. 17, paragraph 4; p. 18, paragraph 1; p. 30, paragraphs 3-4; p. 31, paragraph 2 (Reference in Russian and English Translation).
Shak et al., Recombinant human DNAse I reduces the viscosity of cystic fibrosis sputum, Proc. Natl. Acad. Sci. USA, vol. 87, pp. 9188-9192, 1990.

(56) References Cited

OTHER PUBLICATIONS

Sherry et al., Presence and Significance of Desoxyribose Nucleoprotein in the Purulent Pleural Exudates of Patients, Proc, Soc. Exp. Biol. Med., pp. 179-184, 1948.
Shevchuk, N.A., Vremyarazreshenniy Immunofluorescentniy Analiz na DNK i Issledovanie Soderzhaniya DNK v Syvoroike Cheloveka, Voprosi Medicinskoi Khimii, No. 4, 2001 (Reference in Russian and English Translation).
Shimony et al., Cell free DNA detected by a novel method in acute ST-elevation myocardial infarction patients, Acute Cardiac Care, vol. 12, pp. 109-111, 2010.
SIGMA Product Information sheet for Deoxyribonuclease I from Bovine Pancreas, 2006.
Simpson G., et al., Successful treatment of empyema thoracis with human recombinant deoxyribonuclease, Thorax, vol. 58, pp. 365-366, 2003.
Supplementary European Search Report for European Patent Appl. No. EP06843990, dated Nov. 23, 2009 and cf Form 1507.
Supplementary European Search Report for European Patent Appl. No. EP04748955, mailed May 19, 2009.
Supplementary European Search Report for European Patent Appl. No. EP04775224, mailed Oct. 28, 2009.
Supplementary European Search Report for European Patent Appl. No. EP05745412, dated Jul. 10, 2009.
Supplementary European Search Report for European Patent Appl. No. EP03796243, dated Jan. 12, 2010.
Tetz VV and Tetz GV, Effect of Extracellular DNA Destruction by DNase I on Characteristics of Forming Biofilms, DNA and Cell Biology, vol. 29, pp. 399-405, 2010.
Tetz, GV, et al., Effect of DNase and Antibiotics on Biofilm Characteristics, Antimicrobial Agents and Chemotherapy, vol. 53, pp. 1204-1209, 2009.
Tetz, GV, et al., Effect of nucleolytic, proteolytic, and lipolytic enzymes on transfer of antibiotic resistance genes in mixed bacterial communities, Universal Journal of Medicine and Dentistry, vol. 1, pp. 46-50, 2012.
Translation of International Preliminary Report on Patentability for PCT/RU2003/000304, dated Nov. 1, 2005.
Translation of International Preliminary Report on Patentability for PCT/RU2004/000260, mailed Jan. 14, 2006.
Translation of International Preliminary Report on Patentability for PCT/RU2004/000261, mailed Dec. 2, 2005.
Translation of International Preliminary Report on Patentability for PCT/RU2004/000262, mailed Apr. 12, 2006.
Translation of International Preliminary Report on Patentability for PCT/RU2006/000642, dated Jul. 7, 2009.
Ulrich & Friend, Toxicogenomics and drug discovery: will new technologies help us produce better drugs? Nature, vol. 1, pp. 84-88, 2002.
Varidase product information from EPGOnline, accessed on Dec. 12, 2011.
Vonmoos, P.L. and Straub, P.W., Absorption and hematologic effect of streptokinase-streptodornase (varidase) after intracavital or oral administration, Schweiz Med Wochenschr, vol. 109, pp. 1538-1544, 1979, Abstract.
Whitchurch, et al., Extracellular DNA Required for Bacterial Biofilm Formation, Science, vol. 295, p. 1487, 2002.
Yasuda, Toshihiro et al., Activity Measurement for Deoxyribonucleases I and II with Picogram Sensitivity Based on DNA SYBR Green I Fluorescence, Analytical Biochemistry, vol. 255, pp. 274-276, 1998.
Ye et al., Quantification of Circulating Cell-Free DNA in the Serum of Patients with Obstructive Sleep Apnea-Hypopnea Syndrome, Lung, vol. 188, pp. 469-474, 2010.
Zaman, et al., Direct amplification of *Entamoeba histolytica* DNA from amoebic liver abscess pus using polymerase chain reaction, Parasitol. Res., vol. 86, pp. 724-728, 2000.
Zaravinos et al., Levosimendan reduces plasma cell-free DNA levels in patients with ischemic cardiomyopathy, J. Thromb. Thrombolysis, vol. 31, pp. 180-187, 2011.
Zhong et al., Presence of mitochondrial tRNA(leu(UUR) A to G 3243 mutation in DNA extracted from serum and plasma of patients with type 2 diabetes mellitus, J. Clin. Pathol., vol. 53, pp. 466-469, 2000.

\* cited by examiner

METHOD FOR TREATING A REDUCTION OF FERTILITY

TECHNICAL FIELD

The invention relates to medicine and veterinary and can be used for increasing longevity and retarding unhealthy manifestations brought by ageing.

BACKGROUND ART

Various methods for retarding ageing are known, said methods are based on the application of antioxidants, immunomodulators, hormones, metabolic modulators (Ann. N.Y. Acad. Sci., 2002; vol. 959); however, the only method for correction (prolongation) of the life span with proven effectiveness is the non-medicamental method of restriction of calorie intake with food (CALORIE RESTRICTION, AGEING, AND CANCER PREVENTION: Mechanisms of Action and Applicability to Humans; Stephen D. et al., Annual Review of Medicine, February 2003, Vol. 54, pp. 131-152).

According to present day notions, the underlying cause of ageing is the loss of the ability to replicate by the somatic cells of the organism during the ageing (Hayflick and Moorhead, 1961, Exp. Cell Res. 25: 585-621; Hayflick, 1965, Exp. Cell Res. 37: 614-636; and Hayflick, 1970, Exp. Geront. 5: 291-303) and the accompanying alteration of the genes expression's profile in ageing cells (West, 1994, Arch. Derm. 130: 87-95), which leads to disturbances of their characteristic functions. Accumulation of such cells in the organs and tissues of the organism that comes with ageing (above all this applies to highly-specialized cells) forms a basis for manifestation of diseases and pathological states typical for an ageing organism.

The reasons behind the loss or perversion of replicative activity of cells brought by ageing are not completely clear yet. According to present day notions the underlying mechanisms may be either those determining the limit of replicative activity of cells, like the exhaustion of telomeres (Harley, 1991, Telomere loss: Mitotic clock or genetic time bomb? Mut. Res. 256:271-282) or the probabilistic mechanisms, for example, the accumulation of somatic mutations in the genome of somatic cells related to ageing (Woodruff R C, et. al., J Anti ageing Med, 2003 Spring 6:pp. 29-39).

In accordance with these notions, the modern medicamental methods for increasing longevity influence the intracellular genetic apparatus of cells. Such are the method of inhibiting the poly enzyme (ADP-ribose) of polymerase (U.S. Pat. No. 5,874,444) and the method of the telomerase enzyme activation (WO2000/31238).

The common disadvantage of methods which utilize active pharmacological intervention on genetic apparatus of ageing cell is the risk of unpredictable side effects (Cellular senescence, ageing and cancer. Campisi J, Scientific World Journal, 2001, Jan. 1 1:1 Suppl 3 65.).

Currently no method exists which allows efficiently retard unhealthy manifestations brought by ageing of human beings. In this connection, it is impossible to choose any known technical solution as a prototype of the present invention.

SUMMARY OF THE INVENTION

It is an object of the present invention to provide a solution for creating an effective method for retarding unhealthy manifestations brought by ageing of human beings (in particular, but not limited to the reduction of sexual activity and fertility, climax, changes in glucose tolerance, reduction of cognitive and mnestic functions, reduction of stress resistance, development of organ and tissue sclerosis) without directly affecting the genetic apparatus of ageing cells.

According to the invention this task is solved by administration into the blood circulation of the agent which inactivates extracellular blood plasma DNA; the extracellular blood DNA inactivating agent can be embodied in the form of an extracellular blood plasma DNA destroying agent; said extracellular blood plasma DNA destroying agent can be embodied in the form of an DNase enzyme; the extracellular blood plasma DNA inactivating agent can also be embodied in the form of an extracellular blood plasma DNA binding agent; the extracellular blood plasma DNA binding agent can be embodied in the form of anti-DNA antibodies; the extracellular blood plasma DNA inactivating agent can be administered in the form of an enzyme modifying the chemical composition of extracellular blood plasma DNA; the extracellular blood plasma DNA inactivating agent can be embodied in the form of an agent that stimulates synthesis or activity of endogenous deoxyribonuclease, or an agent that stimulates the synthesis of antibodies which capable to bind extracellular blood plasma DNA.

The beginning and development of unhealthy manifestations brought by ageing entails qualitative and quantitative alterations of extracellular blood plasma DNA, however, the applicant hasn't found any source of information containing data about genetic repertoire of extracellular blood plasma DNA of patients during ageing, the biological role of the extracellular blood plasma DNA during the ageing or about possible therapeutic effect that its destruction may have on the increase of longevity. In applicant's opinion, this enables to conclude that the invention conforms to the criterion "Novelty" (N).

The applicants found that the extracellular blood plasma DNA of patients during ageing contains a repertoire of genes and regulatory genetic elements that has unique qualitative and quantitative composition that differs dramatically from the repertory of DNA defined in the human genome. Unlike the intracellular DNA, the extracellular blood DNA during the ageing mostly contains unique human genes.

The applicants found that the extracellular blood DNA during the ageing exerts a negative influence on the viability of cells of the organism.

The applicants found that the inactivation of the extracellular blood DNA during the ageing slows down the ageing process.

The abovementioned novel features of the invention, which are based on the fundamentally new notions regarding the role of the extracellular blood DNA during the ageing, enable to conclude that the inventive method conforms to the criterion "Inventive Step" (IS).

BRIEF DESCRIPTION OF THE DRAWINGS

This invention is further explained, by way of drawings.

PREFERRED EMBODIMENT

Figure 1:
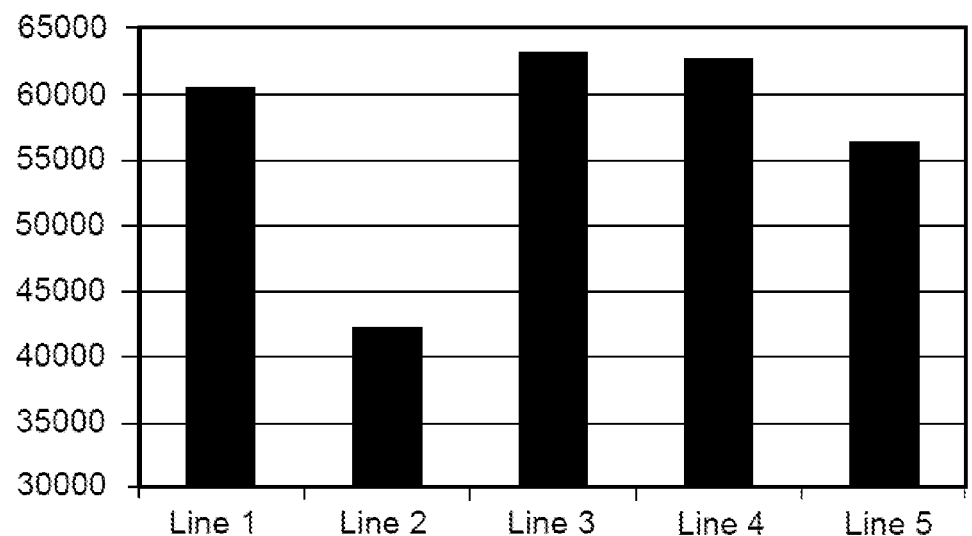
FIG. 1 shows the uptake of [3H] thymidine by cells 48 hours after the passaging in the experiment described in Example 4.

The inventive method is realized in the following way:

Materials and Methods:

The following extracellular blood DNA destroying agents were used: the bovine pancreatic DNAse enzyme (manufactured by Sigma), the recombinant human DNAse I enzyme (manufactured by Genetech), The anti-DNA antibodies extracted from the blood of patients ill with systemic lupus erythematosus according to the A. M. Shuster method (A. M. Shuster et. al., Science, v. 256, 1992, pp. 665-667) were used as the extracellular blood DNA binding agent. Such anti-DNA antibodies are not only able to bind the DNA, but also to hydrolyze it.

The antiG-f actin antibodies (manufactured by Calbiochem) were used as the agent that stimulates the synthesis and/or activity of endogenous biopolymers that bind or destroy or alter the chemical composition and/or conformation and/or polymery of the extracellular blood DNA without destroying it. The G-Actin inhibits the activity of the endogenous DNAse I. The binding of actin by the antibodies increases the activity of the endogenous DNAse I.

The bacterial Sss I Methylase (CpG Methylase) (manufactured by NewEngland Biolabs) was used as the DNA-altering agent. During the experiments the Sss I Methylase was integrated with small unilamellar vesicles (SUV) in the proportion of 1 u of the enzyme per 1 mkg of the lipids (enzymosomes).

The DNA of the blood plasma was extracted in the following way: fresh (no more than 3-4 hours after the sampling) blood plasma with added anticoagulant (sodium citrate) was centrifuged on Ficoll-PlaquePlus (manufactured by Amersham-Pharmacia) during 20 minutes at 1,500 g at room temperature. The plasma was carefully detached (½ of total amount), without affecting the rest of cells on the Ficoll pillow, and further centrifuged at 10,000 g during 30 minutes, in order to remove cell fragments and debris. The supernatant was detached without affecting the sediment, and was toped up to 1% of sarcosil, 50 mM tris-HCl, pH 7.6, 20 mM EDTA, 400 mM NaCl, and then mixed with equal volume of phenol-chloroform 1:1 mixture. The prepared emulsion was incubated during 2 hours at 65° C., then phenol-chloroform mixture was separated by centrifuging at 5,000 g during 20 minutes at room temperature. The procedure of deproteinisation with phenol-chloroform mixture was repeated in the identical way three times, whereupon the aqueous phase was processed first with chloroform, then with diethyl ether. Separation from organic solvents was made by centrifugation at 5,000 g during 15 minutes. The resulting aqueous phase had an equal volume of izopropanol added therein and then the mixture was incubated overnight at the temperature of 0° C. After sedimentation the nucleic acids were separated by centrifugation at 0° C., 10,000 g during 30 minutes. The sediment of nucleic acids was dissolved in the buffer containing 10 mM of tris-HCl, pH 7.6, 5 mM of EDTA, and deposited on the pillow made of cesium chloride gradient (1 M, 2.5M, 5.7M) in a centrifuge tube for rotor SW60Ti. The volume of DNA solution was 2 ml, the volume of each step of CsCl was 1 ml. The ultracentrifugation was done in the L80-80 centrifuge (manufactured by Beckman) during 3 hours at 250,000 g. DNA was collected from the surface of the 5.7M step into fractions. These fractions were dialyzed during 12 hours at 4° C. The presence of the DNA in the fractions was determined by means of agar electrophoresis, with visualization of the DNA by means of the bromide ethidium staining. The amount of the DNA was determined by spectrophotometer (Beckman DU70) in cuvet with volume of 100 mcl at wavelength of 200-320 nm.

EXAMPLE 1

Slowing Down of the Biological Ageing of Human Beings

The bovine pancreatic Dornase enzyme was used as the extracellular blood DNA inactivating agent. 10 clinically healthy men from 50 to 55 took part in the research. Before the beginning of the research the participants were randomly divided into the test group (5 men) and the reference group (5 men). The men of the test group received capsules with the bovine pancreatic Dornase, 900,000 Kuntz Units per day (5 capsules 100 mg each), every day during 6 months. The men of the reference group received 5 capsules with placebo every day during 6 months.

The DNA-hydrolytic activity in the daily urine and the content of the extracellular blood DNA were investigated. Before the beginning of the research and at its completion the biological age (BA) of the participants was determined according to the following method (see Gerontology, 1999, issue 2 "QUALITATIVE EVALUATION OF THE INDICES OF MORTALITY, AGEING, LONGEVITY AND BIOLOGICAL AGE" A. A. Podkolzin, V. N. Krutko, V. I. Dontsov: Institute of System Analysis of Russian Academy of Science, Moscow, National Center of Gerontology, Moscow, Moscow State Medico-Stomatological University of Ministry of Health of Russian federation):

$$BA=26.985+0.215*SBP-0.149*OC-0.151*BI+0.723*HI,$$

where: SBP—systolic blood pressure;

OC—oxygen consumption (time interval between breaths, sec);

BI—time of static balancing, sec;

HI—index of subjective estimate of health (in the present research taken as 0.75).

The results of the research are shown in Table 1.

TABLE 1

Parameters of the biological age of human beings

| Parameter | Test group | Reference group |
|---|---|---|
| DNA-hydrolytic activity in the urine* | +++ | − |
| Extracellular DNA of the blood plasma at the beginning of the research** | 100% | 100% |
| Extracellular DNA of the blood plasma at the end of the research | 75% | 100% |
| Biological age at the beginning of the research | 57.5 | 56.2 |
| Biological age at the end of research | 56.5 | 57.9 |

*The presence of DNA-hydrolytic activity in the urine indicates that large quantities of the Dornase enzyme entered the blood.
**The averaged parameter of quantity of the extracellular blood DNA, determined by measuring the fluorescence of bromide ethidium in the plasma, is taken as 100%.

Thus, the application of the inventive method improves the parameters of biological age of human beings.

EXAMPLE 2

Postponement of Age-Related Death

The stem cells of human umbilical blood (SCUB), transfected in vitro with the DNA of the gene coding for human deoxyribonuclease I, were used as an agent that stimulates synthesis of endogenous deoxyribonuclease.

The experiment was conducted on 40 white outbred rats. The rats in the test group 1 (10 animals), starting from the age of 24 months, were treated by intravenous administration of transfected SCUB, 50,000,000 cells per one animal per infusion, once a month, monthly, until the animal' death. The rats of the test group 2, starting from the age of 24 months, were treated by subcutaneous administration of the calf thymus DNA, once a month, 50 mg per one animal per injection, until the animal death. The rats in the reference group 1 (10 animals) were treated with not transfected SCUB. The rats in the reference group 2 (10 animals) were treated with sodium chloride. The longevity of rats from the reference group 1 averaged to 29 months. The longevity of rats from the reference group 2 (natural longevity) averaged to 27 months. The longevity of rats in the test group 1 averaged to 35 months, in the test group 2 it averaged to 33 months.

EXAMPLE 3

Increase of the Longevity

The bovine pancreatic DNAse enzyme (Sigma), conjugated with the polymer of sialic acid with molecular weight of 36 kDA, was used during the experiment. The experiment was conducted on 24-month old white randomly bred rats. The rats in the test group (15 animals), starting from the age of 24 months, were treated with above said preparation at 500 mg/kg per injection, intravenously, twice a week, during 2 months. The rats of the reference group (15 animals) were treated with phosphate buffer. The longevity of rats in the reference group to 27.8 months. The longevity of rats in the test group averaged to 30.1 months.

Therefore, the destruction of the extracellular blood DNA by the DNAse enzyme slows down the process of ageing according to the inventive method.

EXAMPLE 4

Application of the DNAse for Preventing the Negative Influence of the Extracellular Blood DNA of an Aged Donor on the Viability of Cells During the experiment a line of fibroblasts subcultivated from bioptic material of a healthy 73-year old man was used. The cells were cultivated without adding antibiotics in a minimal essential medium (MEM) with addition of 2 mM of glutamine and 10% of embryonic calves' serum. For the experiment the cells were plated in the amount of 10,000 of cells per $cm^2$ of the surface in the Petri dish and grown in the atmosphere of 5% CO2 at 37° C. The activation of [3H] thymidine was used for determining the intensity of the DNA synthesis during the initial stage of the growth. At the second day after the plating the cultures had [3H] thymidine added to them until reaching the final concentration of 0.1 mCi/ml and then the cells were incubated during 24 hours more, whereupon they were washed off and dissolved in formamide, and their radioactivity was measured.

In the first line (6 dishes) the cells were cultivated without adding the DNA.

In the second line (6 dishes) the extracellular DNA extracted from the blood of the donor was added to the incubating medium in the concentration of 0.005 mkg/ml.

In the third line (6 dishes) the extracellular DNA extracted from the blood of a young healthy volunteer 24 years old was added to the incubating medium in the concentration of 0.005 mkg/ml.

In the fourth line (6 dishes) the extracellular DNA extracted from the blood of the donor in the concentration of 0.005 mkg/ml and the recombinant Dornase-alpha (manufactured by Genetech) in the concentration of 0.5 mkg/ml were added to the incubating medium.

In the fifth line (6 dishes) the recombinant Dornase-alpha (manufactured by Genetech) in the concentration of 0.5 mkg/ml was added to the incubating medium.

The results of the experiment are shown in FIG. 1.

The activation of the [3H] thymidine by the cells 48 hours after the passing.

Thus, the extracellular DNA of the blood plasma of an aged donor has a negative influence on the synthesis of the DNA in the cells. The destruction of the extracellular DNA of the patient's blood by means of the DNAse enzyme counteracts this influence according to the inventive method.

EXAMPLE 5

The Use of Binding and Alteration for Preventing the Negative Influence of the Extracellular Blood DNA of an Aged Donor on the Viability of Cells During the experiment a line of fibroblasts subcultivated from bioptic material of a healthy 73-year old man was used. The cells were cultivated without adding antibiotics in a minimal essential medium (MEM) with addition of 2 mM of glutamine and 10% of embryonic calves' serum. For the experiment the cells were plated in the amount of 10,000 cells per $cm^2$ of the surface in the Petri dish and grown in the atmosphere of 5% $CO_2$ at 37° C. The activation of [3H] thymidine was used for determining the intensity of the DNA synthesis during the initial stage of the growth. At the second day after the plating the cultures had [3H] thymidine added to them until reaching the final concentration of 0.1 mCi/ml and then the cells were incubated during 24 hours more, whereupon they were washed and dissolved in formamide, and their radioactivity was measured.

In the first line (6 dishes) the cells were cultivated without adding the DNA.

In the second line (6 dishes) the extracellular DNA extracted from the blood of the donor was added to the incubating medium in the concentration of 0.005 mkg/ml.

In the third line (6 dishes) the extracellular DNA extracted from the blood of a young healthy volunteer 24 years old was added to the incubating medium in the concentration of 0.005 mkg/ml.

In the fourth line (6 dishes) the extracellular DNA extracted from the blood of the donor in the concentration of 0.005 mkg/ml and the anti-DNA antibodies in the concentration of 5 mkg/ml were added to the incubating medium.

In the fifth line (6 dishes) the extracellular DNA extracted from the blood of the donor in the concentration of 0.005 mkg/ml and the enzymosomos in the concentration of 20 mkg/ml was added to the incubating medium.

Figure 2:
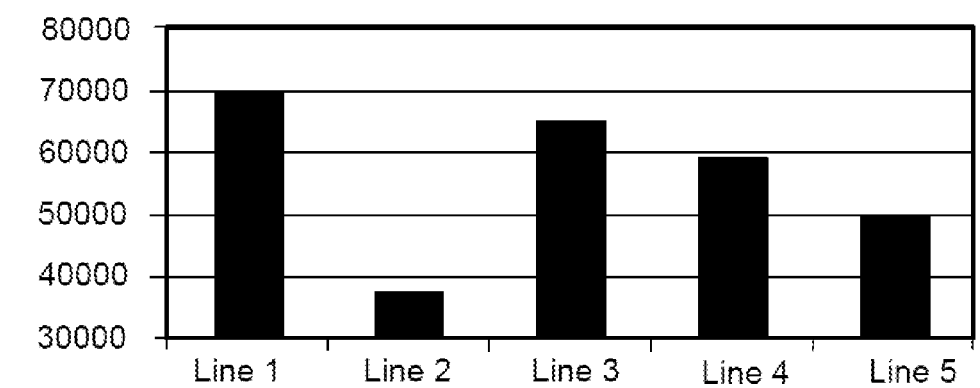
FIG. 2 shows the uptake of [3H] thymidine by cells 48 hours after the passaging in the experiment described in Example 5.

The results of the experiment are shown in FIG. 2.

The activation of the [3H] thymidine by the cells 48 hours after the passaging.

Thus, the extracellular DNA of the blood plasma of an aged donor has a negative influence on the synthesis of the DNA in the cells. The binding and alteration of the extracellular DNA of the patient's blood counteracts this influence according to the inventive method.

EXAMPLE 6

Prevention of the Reduction of Reproductive Ability Brought by Ageing

The experiment was conducted on 20-month old males of mice of the C57Bl line. The males in the test group (9 mice), from the age of 18 months, had intravenous injections of the fraction of mouse antiG-f antibodies (manufactured by Calbiochem) in the amount of 200 mkg per mouse administered to them once a week, every week during 8 weeks. The 9 mice of the reference group had intravenous injections of phosphate buffer. At the age of 20 months the males of the test and the reference groups were put into cells, 3 males per one cell, whereupon 2-month old female mice of the C57Bl were introduced (3 females per one cell). After one week the females were transferred to separate cells and after 23 days more the amount of viable progeny was evaluated for the test and the reference groups. Additional reference was provided in the form of 10 5-month old males of the C57Bl line that mated with 2-month old females of the same line.

The results are shown in Table 2.

TABLE 2

Number of viable progency

|  | Young males | Test group | Reference group |
|---|---|---|---|
| Number of baby mice | 55 | 42 | 24 |

Therefore, the introduction of an agent that suppresses the endogenous inhibitor of its own DNAse I, the biopolymer that destroys the extracellular blood DNA, slows down the reduction of reproductive ability brought by ageing.

EXAMPLE 7

The Prevention of the Weakening of Immunity Brought by Ageing

The experiment was conducted on 20-month old males of mice of the C57Bl line. The males in the test group (10 mice), from the age of 18 months, had intravenous injections of the fraction of human anti-DNA antibodies (manufactured by IgG) in the amount of 200 mkg per mouse administered to them once a week, every week during 8 weeks. The males of the reference group (10 mice) had intravenous injections of phosphate buffer. At the age of 20 months the males of the test and the reference groups each had 30 mkg of virus protein (influenza, strain PR8) introduced subcutaneously, whereupon the antibody titer was evaluated, 15 days after the immunization. Additional reference was provided in the form of 10 5-month old males of the C57Bl line.

The results are shown in Table 3.

TABLE 3

Immunity parameters

|  | Young males | Test group | Reference group |
|---|---|---|---|
| Antibody titer | 300+/−87 | 950+/−191 | 370+/−124 |

Therefore, the introduction of an agent that binds the extracellular blood DNA slows down the weakening of the immunity brought by ageing.

EXAMPLE 8

Slowing Down of the Reduction of Motor Activity Brought by Ageing

The experiment was conducted on 20-month old males of mice of the C57Bl line. The males in the test group (10 mice), from the age of 19 months, had intramuscular injections of the liposomal DNAse I (200 μg of DNAse I in 100 mkg of the mixture of soya phosphatidylcholine and cholesterol (7:3)) administered to them daily. The males of the reference group (10 mice) had intramuscular injections of "empty" liposomes of the same composition. At the age of 20 months the mobility of the animals was measured, by means of one video-recorded observation during 30 minutes with subsequent computer processing. Additional reference was provided in the form of 10 5-month old males of the C57Bl line. The 30-minute activity of 5-month old mice was taken as 100%.

The results are shown in Table 4.

TABLE 4

Parameters of the motor activity

|  | Young males | Test group | Reference group |
|---|---|---|---|
| Mobility | 100% | 70% | 40% |

Therefore, the introduction of an agent that destroys the extracellular blood DNA slows down the reduction of locomotor activity brought by ageing.

INDUSTRIAL APPLICABILITY

The inventive method is realized by means of easy-to-obtain components and known equipment. In applicant's opinion, this enables to conclude that the invention conforms to the criterion "Industrial Applicability" (IA).

The invention claimed is:

1. A method for treating a reduction of fertility in a subject in need thereof, said method comprising administering to said subject a DNase enzyme in therapeutically effective doses and regimens which destroy extracellular blood DNA in the blood of said subject.

2. The method according to claim 1, wherein reduction of fertility is reduction of fertility of subject's semen.

3. The method of claim 1, wherein DNase is administered orally.

4. The method of claim 1, wherein DNase is administered intravenously.

5. The method of claim 1, wherein DNase is administered intramuscularly.

* * * * *